United States Patent [19]

Günther et al.

[11] Patent Number: 5,008,394
[45] Date of Patent: Apr. 16, 1991

[54] PROCESS FOR PRODUCING EBSELEN IN HIGHLY PURE FORM

[75] Inventors: Bernd-Rainer Günther, Bergheim; Rainer Losch, Bonn; Klaus Steiner, Pulheim, all of Fed. Rep. of Germany

[73] Assignee: A. Nattermann & Cie, GmbH, Koln, Fed. Rep. of Germany

[21] Appl. No.: 391,890

[22] Filed: Aug. 9, 1989

[30] Foreign Application Priority Data

Aug. 10, 1988 [DE] Fed. Rep. of Germany ....... 3827093

[51] Int. Cl.$^5$ ............................................. C07D 293/12
[52] U.S. Cl. ................................................... 548/121
[58] Field of Search ........................................ 548/121

[56] References Cited

U.S. PATENT DOCUMENTS 4,711,961 12/1987 Welter ................................. 548/121

FOREIGN PATENT DOCUMENTS 3226286 1/1984 Fed. Rep. of Germany ...... 548/121

OTHER PUBLICATIONS

Hirokazv, Bull Chem. Soc. Japan, 59 p. 2181, 1986.

Renson, Bull Soclhim Belg. 73 507 (1961).
Fischer, IBID 96 765 (1987).
N. Dereu, E. Graf; Drugs of the Future, vol. 9, No. 10, S. 741 (1984).
L. Tschugaeff and W. Chlopin, Ber. 47, S. 1269–1275 (1914).
A. Ruwet and M. Beson, Bull. Soc. Chim Belges, 75, S. 157–168 (1966).
R. Lesser and R. Weiß, Ber. 46, S. 2640–2658 (1913).
R. Lesser and R. Weiß, Ber. 57, S. 1077–1082 (1924).

*Primary Examiner*—Robert Gerstl
*Attorney, Agent, or Firm*—Pearne, Gordon, McCoy & Granger

[57] ABSTRACT

The invention is related to a process for preparing highly pure Ebselen (2-phenyl-1.2-benzisoselenazole-3(2H)-one) of formula

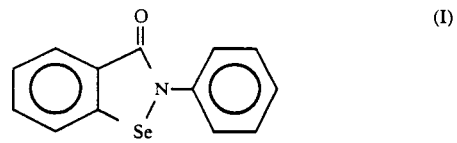

(I)

4 Claims, No Drawings

PROCESS FOR PRODUCING EBSELEN IN HIGHLY PURE FORM

The present invention is related to a procecc for producing Ebselen (i.e. 2-phenyl-1.2-benzisoselenazol-3(2H)-one) of formula I in highly pure form.

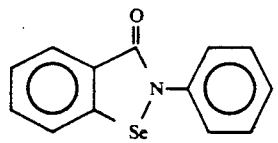

Ebselen is a pharmacologically active and extremly nontoxic organic selenium compound with valuable pharmacological properties, i.e. for instance anti-inflammatoric properties (N. Dereu, E. Graf; Drugs of the Future Vol. 9, No. 10, p. 741 (1984)).

Up to now, Ebselen is prepared as follows:

According to L. Tschugaeff and W. Chlopin, Ber. 47, pgs. 1269 to 1275 (1914), selenium is reduced with sodium formaldehyde sulfoxylate (Rongalit) in an alkaline aqueous solution thereof at temperatures of 70° to 80° C. The resulting sodium diselenide is separated by crystallisation upon cooling of the resulting mother liquor; the resulting sodium diselenide is subjected to reaction with diazotized anthranilic acid (o—N N—$C_6H_4$—COOH) at a temperature below 10° C. in aqueous alkaline solution, in accordance with A. Ruwet and M. Reson, Bull. Soc. Chim Belges, 75, pgs. 157 to 168 (1966); the resulting solution is clarified with activated charcoal for absorption of red collodial selenium; the resulting solution is acidified and the resulting o-diselenosalicylic acid is filtered off. This product is obtained in a yield of 50 to 90%. o-Diselenosalicylic acid thereafter is heated with a surplus of thionylchloride while refluxing, in accordance with R. Lesser and R. Weiss; Ber. 46, pgs. 2640 to 2658 (1913). The surplus thionylchloride is removed and the resulting product is extracted with petrol ether and, finally, the resulting o-chlorselenobenzoic acid chloride is subjected to reaction with aniline in benzene with ice cooling, in accordance with R. Lesser and R. Weiss; Ber. 57, pgs. 1077 to 1082 (1924).

However, already in the first step of this know process, a o-diselenosalicylic acid product is obtained which is highly contaminated with the monoselenide (i.e. 2.2'-selenobisbenzoic acid), the triselenide and amorphous selenium, and it is difficult to seperate this highly contaminated product by suction or centrifugation. In addition thereto, the reaction of the thus obtained o-diselenosalicylic acid with thionylchloride to yield o-chloroselenobenzoic acid chloride necessitates a burdensome recrystallisation of the poisonous o-chloroselenobenzoic acid chloridedifficult to handle. Further, the preparation of Ebselen known up to now does not allow to produce this compound in sufficient amounts and with sufficient purity by procedures easy to practice.

Since pharmaceutical products in particular have to be highly pure products, it is an object of the present invention to develope a procedure by which Ebselen in a simple, easy and cheap procedure may be produced yielding into a product of high purity.

The process of the present invention is based upon the known reduction of metallic selenium by means of sodium formaldehyde sulfoxylate (Rongalit) in aqueous alkaline solutions to yield sodium selenide, reacting the resulting sodium selenide with diazotized anthralinic acid in alkaline solution to yield the sodium salt of o-diseleno salicylic acid, converting the free o-diseleno salicylic acid with thionylchloride in excess to yield o-chloroselenobenzoic acid chloride and subjecting this chloroselenobenzoic acid chloride with aniline in an organic solvent.

The process of the present invention is characterised in that, (a) the reduction of the metallic selenium in soda lye with Rongalit is effected at a temperature between 20° and 50° C. and the reaction mixture after having added all reaction components is kept at the applied reaction temperature for another period of 0.5 and 2 hours, (b) the resulting alkaline sodium selenide solution immidiately thereafter is subjected to reaction with diazotized anthranilic acid between 0° and 10° C. for 1 to 2 hours, the resulting alkaline o-diselenosalicylic acid solution is rendered to a pH value between 7.5 to 8.5 by the addition of acetic acid, the resulting solution is clarified as soon as it becomes turbid and is treated with activated charcoal and, for separating the activated charcoal, the solution is rendered to a pH between 5 and 6 by the addition of acetic acid and the precipitated separated pure o-diselenosalicylic acid still moist with water is mixed with a solvent selected from the group of 1.2-dichloroethane, chloroform, tetrachloroethane or petrolether, preferably 1.2-dichloroethane and this mixture is heated to boiling at a water separator until all of the water has been distilled off azeotropically, (c) o-diselenosalicylic acid obtained in step (b) and suspended in the used solvent in a finely divided form is subjected to reaction with thionylchloride in the presence of a catalytic amount of dimethylformamide, the solvent and excess thionylchloride is distilled off from the reaction mixture, possibly still present thionylchloride is removed by at least adding twice the used solvent and distilling off the same and (d) the purified o-chlorselenobenzoic acid chloride obtained in step (c) is dissolved in a solvent selected from the group consisting of 1.2-dichloroethane, chloroform, tetrachloroethylene and diisopropylether, preferably 1.2-dichloroethane, and, with careful stirring, the resulting solution is poured into a suspension of aniline in dilluted soda lye; and the precipitated reaction product is separated with filtration, is washed until neutral and is dried.

The dried Ebselen preferably is recrystallized from 1.2-dichloroethane or butanone-2. Ebselen moist of water may be recrystallized directly from 1.2-dichloroethane after azeotropic distillation with 1.2-dichloroethane. Small amounts of —$Se_xS_y$—(x=1 to 8; y=7 to 0) and amorphous selenium as impurities of the resulting reaction product may be removed by treatment thereof with solid sodium hydroxide and activated carbon in 1.2-dichloroethane.

Very important for the new process for producing Ebselen is the fact that the reaction is carried out in a two-phase aqueous-alkaline reaction medium admixed with a solvent from the group of 1.2-dichloroethane, chloroform, tetrachloroethylene and diisopropylether as organic phase and that the resulting o-chloroselenobenzoic acid chloride dissolved in such a solvent is added to an aqueous suspension of freshly distilled aniline in dilluted soda lye during a period of about 1 to 1.5 hours at a temperature of about 20° to 25° C. with careful stirring. The selection of the reaction vessel and of the stirrer has to be effected such that during the stirring no emulsion is formed by vertical stirring powers. Further substantial for the new process is the fact that after carrying out the reaction, the resulting Ebselen is separated as soon as possible and is washed to neutral state.

Surprisingly, when effecting the process of production in this way there is observed a decomposition of Ebselen to the diselenide compound of formula IV only in a low amount.

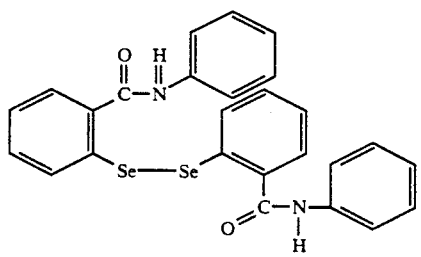
(IV)

Furthermore, it is essential for the process of the present invention that the dried Ebselen is recrystallized from butanone-2 or 1.2-dichloroethane and is possibly treated with solid sodium hydroxide and activated charcoal in 1.2-dichloroethane and that the Ebselen still moist with water is first subjected to cyclic azeotropic distillation and immediately thereafter is recrystallized from 1.2-dichloroethane. Surprisingly, following this way, there is obtained a highly purified Ebselen free from the diselenid compound, —$Se_xS_y$— and amorphous selenium.

The process for producing Ebselen in accordance with the present invention is further illustrated by the following examples.

EXAMPLE 1

I. 12.0 kg of demineralized water are given into a 180 ltr. reaction vessel. Thereafter, 3.15 kg (40 mole) of selenium, black 99.5% are added thereto with stirring. With further stirring there are added 21.95 kg (137.2 mole) of 25% aqueous soda lye and, thereafter 3.43 kg (21.6 mole) of about 97% Rongalit. There is obtained a dark brown solution. When adding Rongalit, the temperature is raised to 35° to 50° C. The reaction mixture is further heated to 45° C. by the heating case of the reaction vessel and stirred for another 1 to 2 hours.

II. Into a reaction vessel which may be cooled from outside and which is equipped with a stirrer there are added 6 kg of ice and 10.6 kg (93.2 mole) of 32% aqueous hydrochloride acid. 5.6 kg (40.0 mole) of about 97% anthranilic acid are added to this solution with stirring. A solution of 2.9 kg (41.4 mole) of more than 98% sodium nitrite is dissolved in 6.8 kg of demineralized water. With cooling to 0° to 5° C., this solution is added dropwise during a period of 1.5 to 2 hours. The solution of the diazonium salt has to be stored at 0° to 5° C. until completely used.

III. The selenide solution from I is cooled to 10° C. With cooling the diazonium salt solution obtained according to II is added to this solution during a period of 1.5 to 2 hours such that the temperature in the reaction medium always is below 10° C. The pH of the solution during the complete reaction time has to be equal to or higher than 10. After completion of the addition, the reaction mixture is stirred for further 1 to 2 hours without cooling.

IV. With stirring and by careful dropwise addition of about 2.5 to 3 kg (about 6 mole) of dilute acetic acid (120 g per l) the pH of the reaction mixture is brought to 8.5 and the reaction mixture is cleared by filtration.

V. Thereafter, the solution is stirred for 2 hours at a temperature of 20° C. to 25° C. with 0.8 kg of activated charcoal and it is clarified by filtration through a filter with pressure. The resulting reaction product is precipitated with continuous careful control of its pH at room temperature (20° C. to 25° C.) with the addition of about 33 kg (about 66 mole) of dilute acetic acid (120 g per l) in the reaction vessel. Thereafter, the product is brought to pH 5.0 to 5.5 by addition of acetic acid, is stirred from 30 minutes and the pH is again rendered to the above value. This treatment is continued until a constant pH value. Finally, the reaction product is mixed with about 3.3 kg of about 98% acetic acid and brought to a pH of 4.2 to 4.5. The precipitated product is filtered with suction.

Yield of first precipitation: 6.64/7.5 kg of dry material.

VI. The moist o-diselenosalicylic acid is suspended in about 60 kg of demineralized water. There are added to this suspension dropwise about 5.1 kg (about 32 mole) of 25% soda lye until a pH of 12.5 is reached. The resulting red cloudy solution obtained thereby is mixed with about 1 kg of dilute acetic acid (120 g/l) to yield a pH of 5.0 to 5.5. The turbid solution is filtered with suction. The clarified filtrate is mixed with about 1 kg of dilute acetic acid (120 g/l) yielding again a pH of 8.5. The solution is stirred with 0.8 kg of activated charcoal for 1.5 hours. The solution containing charcoal is filtered. The resulting product is precipitated from the clarified solution by the addition of about 15 kg (about 30 mole) of dilute acetic acid (120 g/l). The precipitated product is filtered with strong suction. The filter cake is stirred with about 32 kg of water acidified with acetic acid to a pH of 4.5 and thereafter it is filtered with suction another time.

Yield of second precipitation: 6.5 kg of dry material.

EXAMPLE 2

4.5 kg (11.24 mole) of moist o-diselenosalicylic acid is given into a heatable glas vessel having a volume of 45 ltr., equipped with a stirrer, a internal thermometer, a distillation bridge with ascending cooler and a T-piece with faucet between cooler and vessel and an exchangeable collector vessel, and absorption tower. 17.7 kg (14.2 ltr.) of chemically pure 1.2-dichloroethane are added thereto. Thei mixture is heated with stirring to reflux (inner temperature about 74° C., heating bath temperature about 140° C.). The azeotropic distillate is collected in the exchangeable collector vessel. This yields into a separation of the water azeotropically distilled off. The separated dichloroethane is given back into the reaction vessel. The separated water is weighed and the result is used to determined the dry weight of o-diselenosalicylic acid. Dry weight of o-diselenosalicylic acid=moist o-diselenosalicylic acid less amount of separated water.

The suspension free of water is mixed with 13 ml of dimethylformamide pure for 99% or more. At reflux temperature and with heavy stirring, 5.94 kg (49.45 mole) of thionylchloride (purity for synthesis 99% or higher) is added as quick as possible. The actual amount of added thionylchloride has to be adapted to the above calculated dry weight of o-diselenosalicylic acid (a molar relation of 1:4.4). After the addition of thionylchloride, the reaction mixture is stirred for another hour with reflux (end of gas formation). 1.2-Dichloroethane is distilled off with stirring (bath temperature about 140° C.). Subsequently the product is dried at a water ring vacuum of about 110 mbar. The resulting melt is stirred with 7.1 ltr. (8.9 kg) 1.2-dichloroethane and, subsequently, 1.2-dichloroethane is distilled off as above described. This procedure is repeated another two times. The resulting dark red melt is dissolved in 7.1 ltr. (8.9 kg) of 1.2-dichloroethane and the solution cooled to room temperature. The resulting solution is used for further reaction.

Yield: 5.7 kg dry weight.

EXAMPLE 3

There is used a 45 ltr. glas reaction vessel having a casing for cooling. With cooling, 1.57 kg (39.36 mole) of solid pelleted sodium hydroxide are dissolved in 29 kg of water. 1.83 kg (19.68 mole) of aniline (colourless), purity 99% or more are added at 20° C. With cooling and heavy stirring there are added about 10 ltr. (5.0 kg dry weight) (19.68 mole) of o-chloroselenobenzoic acid chloride solution in 1.2-dichloroethane dropwise within 1 hour at 20° to 25° C. internal temperature. The reaction mixture is stirred for another hour at 20° C. to 25° C. and a pH of 7 to 9.

The precipitated product is filtered with suction, washed twice with about 15 kg of water and dried with suction. The final washing water is to have a pH of 7 to 7.5.

The moist crude Ebselen product is dried in a vacuum drying box at 80° C. and 15 mg Hg until the weight remains equal.

Yield of crude Ebselen: 4.8 kg of dry product.
Recrystallisation from butanone-2:

4.3 kg of dried crude Ebselen product are mixed in a reactor with 86 l of chemically pure butanone-2. The product is dissolved by boiling with reflux and stirring. The slightly turbid solution is mixed with 0.43 kg of activated charcoal after cooling to 70° C. This solution is stirred for 30 minutes with reflux. The clear, slightly yellow filtrated solution is cooled with stirring to 20° C. The precipitate is filtered off with suction and dried in a vacuum dryer until constant weight.

Yield: 3.0 kg dry weight—Mp.: 181° to 183° C.
Recrystallisation from 1.2-dichloroethane:

4.3 kg of dry weight crude Ebselen still moist with water are given to a heatable reactor together with 43 ltr. (53.75 kg) of chemically pure 1.2-dichloroethane. The mix is heated with stirring to reflux temperature. The product is dried by azeotropic distillation and an almost clear solution is obtained. Added thereto is a suspension of 0.43 kg of activated charcoal in 1.2-dichloroethane. The total mix is stirred to reflux for 30 minutes and is thereafter filtered to yield a clear solution. The clear slightly yellow solution is cooled with stirring to about 20° C. The precipitate is filtered with suction and is dried at 60° C. and 15 mm Hg until constant weight.

Yield: 3.27 kg of dry product—M.p.: 181° to 183° C.

EXAMPLE 4

Treatment of Ebselen with Solid Sodium Hydroxide and Activated Charcoal in 1.2-Dichloroethane 20.0 kg Ebselen, 200 ltr. of pure 1.2-dichloroethane, 1.0 kg of granulated sodium hydroxide (product Merck N. 6467) and 2 kg of actived charcoal are given into a 250 ltr. stainless steel reaction vessel at room temperature. The mixture is boiled to reflux with stirring for 2 hours. The hot solution is filtered off at about 80° C. to 90° C. The clear slightly yellow filtrate is cooled with stirring to 20° C. The crystallized precipitate is filtered with suction. The filter cake is further washed with 5 to 7 ltr. of pure 1.2-dichloroethane at 60° C. to 70° C. and the product is dried at 60° C. to 70° C. and 20 to 100 mbar.

Yield: 17 kg (up to 85% of the theoretical).

What we claim is:

1. Process for the production of 2-phenyl-1.2-benzisoselenazole-3(2H)-one (Ebselen) by reduction of metallic selenium by means of sodium formaldehyde sulfoxylate (Rongalit) in aqueous alkaline solution to yield sodium selenide, subjecting of the resulting sodium selenide to reaction with diazotized anthralinic acid in alkaline reaction medium to yield the sodium salt of o-diselenosalicylic acid, subjecting to reaction of the resulting the diseleno salicylic acid with an excess of thionylchloride to yield o-chloroselenobenzoic acid chloride, subjecting to reaction of the resulting chloroselenobenzoic acid chloride with aniline in an organic solvent, wherein (a) the reduction of the metallic selenium in soda lye with Rongalit is effected at a temperature between 20° and 50° C. and the reaction mixture, after having added all reaction components, is kept at the applied reaction temperature for another 0.5 to 2 hours, (b) the resulting alkaline solution of sodium selenide immediately thereafter is subjected to reaction with diazotized anthranilic acid at a temperature between 0° and 10° C. for 1 to 2 hours; the resulting alkaline solution of o-diselenosalicylic acid is mixed with acetic acid to a pH between 7.5 and 8.5, the thus resulting solution is clarified as soon as it becomes turbid and thereafter is treated with activated charcoal and thereafter, for seperating the activated charcoal, the solution is mixed with acetic acid to a pH between 5 and 6, and the precipitated separated pure o-diselenosalicylic acid still moist with water is mixed with 1.2-dichloroethane, and is heated to boiling with a cyclic water separator for such a time, until or of the water has been distilled off azeotropically, (c) the o-diselenosalicylic acid resulting from step (b) and suspended in the used solvent in finely divided form is subjected to reaction with thionylchloride in the presence of catalytic amounts of dimethylformamide; the solvent and the excess thionylchloride is distilled off from the reaction mixture; possibly still present thionylchloride is removed by adding at least twice the used solvent and distilling it off and (d) the purified o-chloroselenobenzoic acid chloride obtained in step (c) is dissolved in 1.2-dichloroethane, and, with careful stirring, the resulting solution is added to a suspension of aniline in dilute soda lye; and the precipitated reaction product is separated, washed until neutral and is dried.

2. Process according to claim 1, wherein the dried Ebselen is recrystallized from 1.2-dichloroethane or butanone-2.

3. Process according to claim 1, wherein the Ebselen product moist with water obtained in step (d) is recrystallized directly from 1.2-dichloromethane after removal of the water by cyclic azeotropic distillation with 1.2-dichloroethane.

4. Process according to claim 2, wherein the Ebselen product moist with water obtained in step (d) is recrystallized directly from 1.2-dichloromethane after removal of the water by cyclic azeotropic distillation with 1.2-dichloroethane.

* * * * *